US006931284B2

(12) United States Patent
Engmark et al.

(10) Patent No.: US 6,931,284 B2
(45) Date of Patent: Aug. 16, 2005

(54) IMPLANTABLE MEDICAL DEVICE WITH AIR CORE ANTENNA ASSEMBLY

(75) Inventors: David B. Engmark, Bethel, MN (US); John E. Nicholson, Blaine, MN (US); Brian S. Child, Phoenix, AZ (US); David M. Reinker, Ponte Vedra Beach, FL (US)

(73) Assignee: Medtronic, Inc., Minneapolis, MN (US)

( * ) Notice: Subject to any disclaimer, the term of this patent is extended or adjusted under 35 U.S.C. 154(b) by 222 days.

(21) Appl. No.: 10/280,944

(22) Filed: Oct. 25, 2002

(65) Prior Publication Data

US 2004/0082977 A1 Apr. 29, 2004

(51) Int. Cl.$^7$ ............................................... A61N 1/375
(52) U.S. Cl. ............................. 607/36; 607/32; 607/60
(58) Field of Search ............................... 607/32, 60, 36

(56) References Cited

U.S. PATENT DOCUMENTS

| | | | | |
|---|---|---|---|---|
| 4,314,562 A | * | 2/1982 | Ware ............................ | 607/36 |
| 4,401,120 A | | 8/1983 | Hartlaub et al. | |
| 4,441,498 A | * | 4/1984 | Nordling ...................... | 607/32 |
| 4,958,632 A | | 9/1990 | Duggan | |
| 5,052,388 A | | 10/1991 | Sivula et al. | |
| 5,080,096 A | | 1/1992 | Hooper et al. | |
| 5,088,488 A | | 2/1992 | Markowitz et al. | |
| 5,127,404 A | | 7/1992 | Wyborny et al. | |
| 5,154,170 A | | 10/1992 | Bennett et al. | |
| 5,456,698 A | * | 10/1995 | Byland et al. ................ | 607/36 |
| 5,535,097 A | | 7/1996 | Ruben et al. | |
| 5,951,594 A | * | 9/1999 | Kerver ......................... | 607/32 |
| 6,115,634 A | * | 9/2000 | Donders et al. .............. | 607/32 |

* cited by examiner

Primary Examiner—Jeffrey R. Jastrzab
Assistant Examiner—Alyssa M. Alter
(74) Attorney, Agent, or Firm—Michael C. Soldner; Girma Wolde-Michael (57) ABSTRACT

An implantable medical device that includes an enclosure, an electrical module for the desired stimulation, sensing and communications functions, a power source, an air-core antenna, and supporting structures therefore. The antenna includes a quarter-elliptical shape that maximizes the antenna area to facilitate transmission of electromagnetic waves through the enclosure. A support structure is provided so that the antenna, the module and the battery self-align with each other and the enclosure. The support structure contains contacts to facilitate electrical connection of the antenna to the module and positions the module so that contacts thereon are in close proximity in plan and elevation to external electrical feed-throughs in the housing and the antenna contacts on the support structure. The support structure positions the antenna between the module and the housing, separated therefrom by a predetermined minimum distance to facilitate efficient coupling of electromagnetic waves to and/or from the antenna.

20 Claims, 6 Drawing Sheets

IMPLANTABLE MEDICAL DEVICE WITH AIR CORE ANTENNA ASSEMBLY

FIELD OF THE INVENTION

This invention is related generally to implantable medical devices, and more particularly to an implantable medical device incorporating an air-core antenna.

BACKGROUND OF THE INVENTION

Implantable medical devices such as pacemakers, defibrillators, neuro-stimulators, and the like are generally deployed in a housing that includes two metal halves forming a "clam-shell" assembly. Other housing materials may also be used. The housing is hermetically sealed after assembly so that body fluids surrounding the implanted device cannot penetrate the housing and disturb the electrical circuitry contained therein. It is generally very important that the housing be as small as possible and usually as flat as possible to make it easy to implant.

One or more feed-through connectors permit electrical communication to and from the electrical components and circuitry contained within the housing while at the same time maintaining the hermeticity of the device. These connections are typically used to test the device and provide electrical stimuli and/or electrical sensing within the body in which the device is implanted. However, in some cases it is desirable to be able to couple electrical signals into or out of the device without making direct electrical contact thereto. Such "non-contact" signals may be used to provide electrical energy to the device and/or send information or program instructions to or from the device either before or after it is implanted. An antenna is provided within the housing to transmit and/or receive such non-contact electrical signals. Relatively low frequency radio waves are commonly used for such purposes.

Various antenna designs have been employed in the past for such purposes. Examples are ferrite loaded coils and non-ferrite loaded coils formed on a circuit board or flexible tape. While such arrangements work, they suffer from a number of disadvantages, for example, excessive size and weight, awkward shapes which make it difficult to integrate the prior art antennas with the other components within the very cramped housing, poor electrical characteristics, and high cost of manufacture and/or assembly within the overall device. These problems are most severe with air-core antennas which, in order to have suitable electrical characteristics, are generally physically larger and, for efficient operation, are spaced apart from the walls of the housing or other significant conductive regions in the housing. The problem of providing an internal air-core antenna is exacerbated by the overriding requirement that the overall size of the implantable device be kept as small as possible and the need to accommodate within the housing, not only the antenna, but a long life battery and the electrical circuitry providing the desired sensing and/or stimulating functions.

For further discussion of implantable devices, as for example, cardiac pacemakers, reference may be made to U.S. Pat. No. 4,401,120 to HARTLAUB et al; U.S. Pat. No. 4,958,632 to DUGGAN; U.S. Pat. No. 5,052,388 to SIVULA et al, U.S. Pat. No. 5,080,096 to HOOPER et al; U.S. Pat. No. 5,088,488 to MARKOWITZ et al; U.S. Pat. No. 5,127,404 to WYBORNY et al; U.S. Pat. No. 5,154,170 to BENNETT et al; and U.S. Pat. No. 5,535,097 to RUBEN et al.

In view of the foregoing, it should be appreciated that there is an ongoing need to provide an improved implantable device having an air-core antenna and an antenna mounting structure that is physically stable, that integrates conveniently with the electrical circuitry, battery and contacts within the housing, that is easy to assemble, and that has appropriate electrical characteristics suitable for the desired application. Additional features will become apparent to one skilled in the art based on the foregoing background of the invention, the accompanying drawings, the following detailed description of a preferred embodiment and the appended claims.

As used herein, the terms "medical device," "implantable device" and "implantable medical device" are intended to refer to a medical device for monitoring or delivering therapy or a combination thereof in a human or animal body.

SUMMARY OF THE INVENTION

According to a first aspect of the inventions, there is provided an implantable medical device for electrically interacting with a surrounding body, comprising, an enclosure at least partially transparent to electromagnetic waves and having an inner surface, within which is an energy source and electrical circuitry coupled to the energy source for providing or receiving electrical signals to or from the body, a multi-layer air-core antenna located within the enclosure and electrically coupled to the electrical circuitry for sending or receiving electromagnetic waves through the enclosure, and a first support member for retaining the antenna in predetermined relation to the enclosure and the electrical circuitry. The support member includes insulating members having an outer surface that conforms at least in part to a portion of the inner surface of the enclosure and electrical contacts for receiving connections from the antenna and the electrical circuitry so that the antenna and electrical circuitry are thereby electrically coupled.

In a further aspect of the invention the support member further comprises a first portion for retaining the antenna in predetermined relation thereto and a second portion for spacing a principal plane of the antenna at least a minimum predetermined distance away from the inner surface of the enclosure. In a still further aspect of the invention the antenna has a substantially quarter-elliptical plan shape. A second insulating member is desirably provided for receiving the energy source, wherein the first and second insulating members have mating alignment regions.

In a still further aspect of the invention, the electrical circuitry is mounted on a substrate and the first support member aligns the antenna with respect to the enclosure and the substrate with respect to the antenna, so that predetermined minimum spacings are maintained between the principal planes of the antenna and principal planes of the substrate and the enclosure. In a yet further aspect of the invention, the antenna is located substantially between the substrate and the enclosure.

BRIEF DESCRIPTION OF THE DRAWINGS

The following drawings are illustrative of particular embodiments and therefore do not limit the scope of the invention. They are presented to assist in providing a proper understanding of the invention. The drawings are not to scale (unless so stated) and are intended for use in conjunction with the explanations in the following detailed description. The present invention will hereinafter be described in conjunction with the accompanying drawings, wherein like referenced numerals denote like elements, and.

DESCRIPTION OF THE PREFERRED EXEMPLARY EMBODIMENTS

Figure 1:
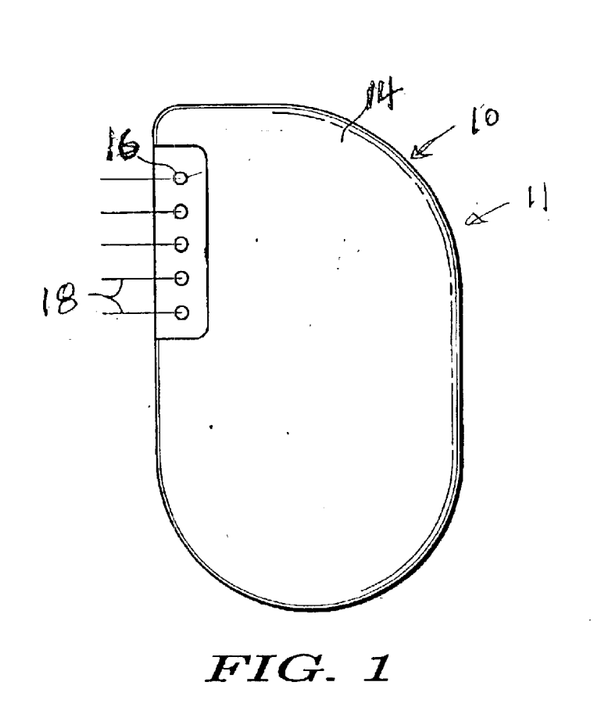
FIG. 1 and FIG. 2 are plan and side views respectively of an assembled implantable medical device.
Figure 2:
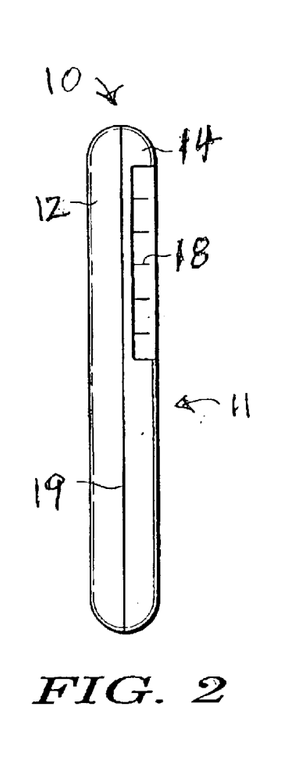

FIG. 1 and FIG. 2 are plan and side views respectively of assembled implantable medical device 10 in accordance with the present invention. Device 10 includes an enclosure or housing 11 having upper half 12, lower half 14, and electrical feed-throughs 16 to which are connected lead wires 18. Ordinarily upper and lower halves 12, 14 of housing 11 are welded together or otherwise sealed at joint 19 so as to be hermetic. The exact manner of sealing housing 11 is outside the scope of this invention. Housing 11 is generally made of titanium or other biocompatible material. Other housing materials can be used so long as they are biocompatible and sufficiently transparent to electromagnetic waves being sent to and/or received from device 10. Wires 18 are conveniently coupled to the organ or organs being monitored and/or stimulated by device 10 by use of a connector (not shown) with lead extensions attached thereto. The connector and lead extensions are outside the scope of the present invention.

Figure 3:
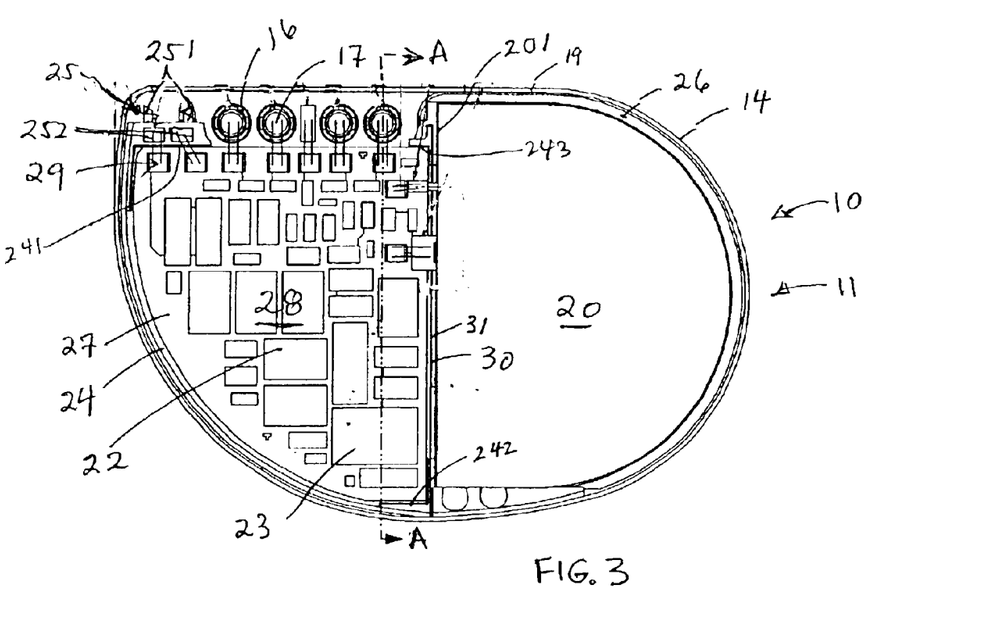
FIG. 3 is a top interior view of the device shown in FIGS. 1–2.

FIG. 3 is a top view of device 10 of FIGS. 1–2 with upper housing half 12 removed so that interior features can be seen. Lower housing half 14 contains energy source 20, typically a battery, electrical circuitry 22 and mounting or support structures 24, 26 for electrical circuitry 22 and battery 20, respectively. Further details of support structures 24, 26 are described in connection with FIGS. 4–5 and 7–8. As used herein, the word "battery" is intended to include any type of power source, as for example but not limited to chemical batteries, capacitive storage devices, and so forth.

Electrical circuitry 22 typically contains numerous interconnected electrical components 23 mounted on circuit board 27 so as to form electrical module 28. As those of skill in the art will understand, the particular design of electrical circuitry 22 will depend upon the electrical function required to be performed by device 10 and will vary from application to application. Thus module 28 is intended to refer to any electrical module for providing the stimulus, communication and/or control functions needed for device 10. Circuit board 27 of module 28 includes metal contact areas 29 that are conveniently electrically coupled to inner portions 17 of one or more electrical feed-throughs 16 of device 10.

Figure 4:
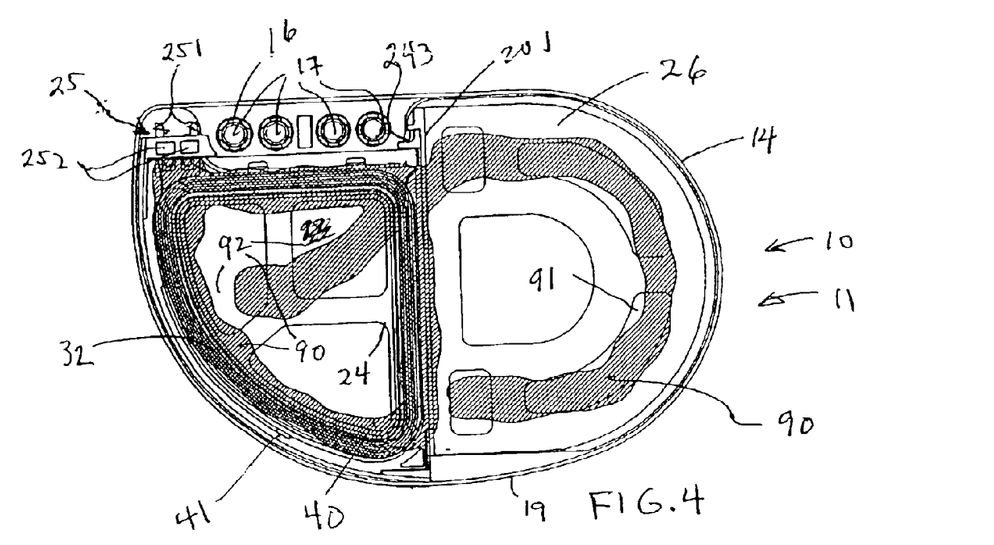
FIG. 4 is a view similar to FIG. 3 but with some interior structure removed to show underlying regions.

FIG. 4 is a view similar to FIG. 3 but with module 28 removed to show antenna coil 32 located in underlying support structure 24 and battery 20 removed to show underlying support structure 26. Electrical contacts 25 are provided on support structure 24 to permit electrical coupling to appropriate portions of contacts 29 on circuit board 27 and to antenna coil 32. Electrical contacts are preferable insert-molded into support 24, for example, molded in place within support 24 so that only external portions 251, 252 of contacts 25 are exposed outside of support 24, but this is not essential. Any convenient means for providing contacts 25 with portions 251, 252 or the like in or on support 24 may also be used.

Figure 5:
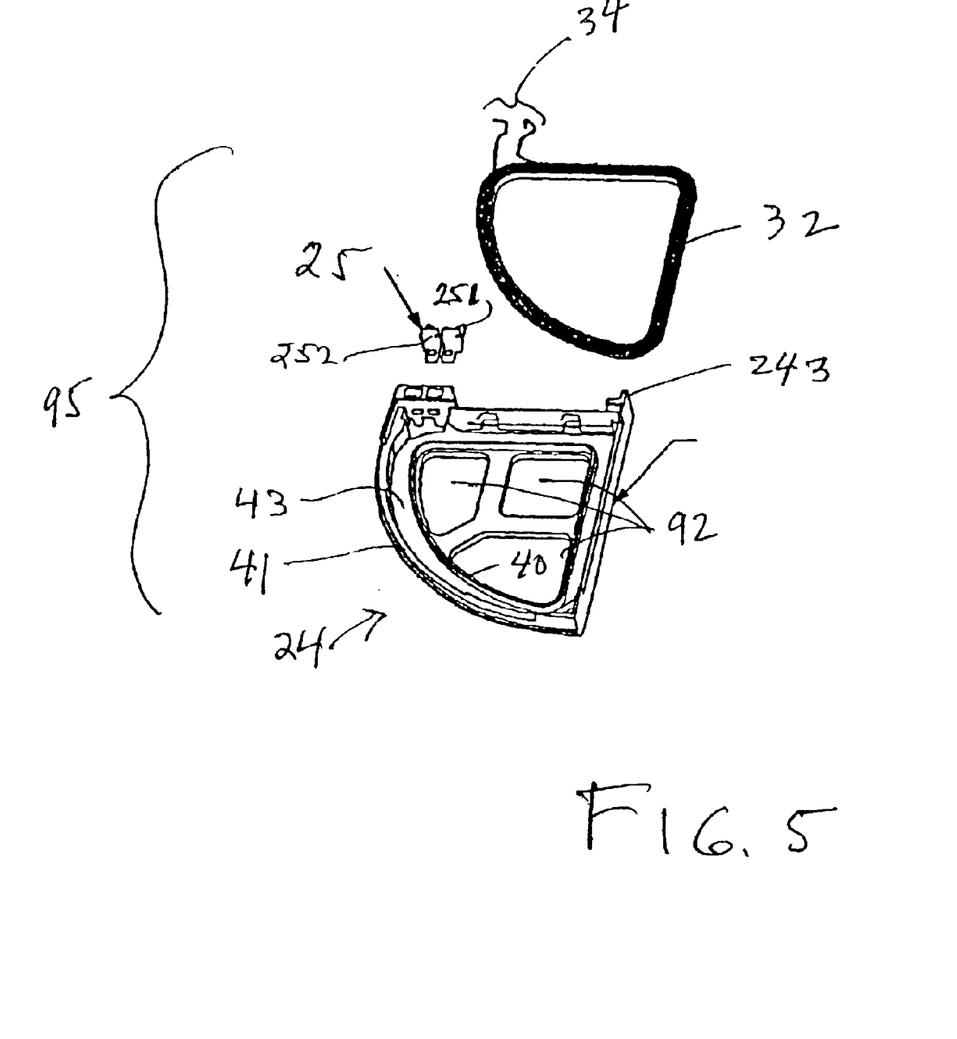
FIG. 5 is a partially exploded perspective view of part of the device of FIG. 4.
Figure 6A:
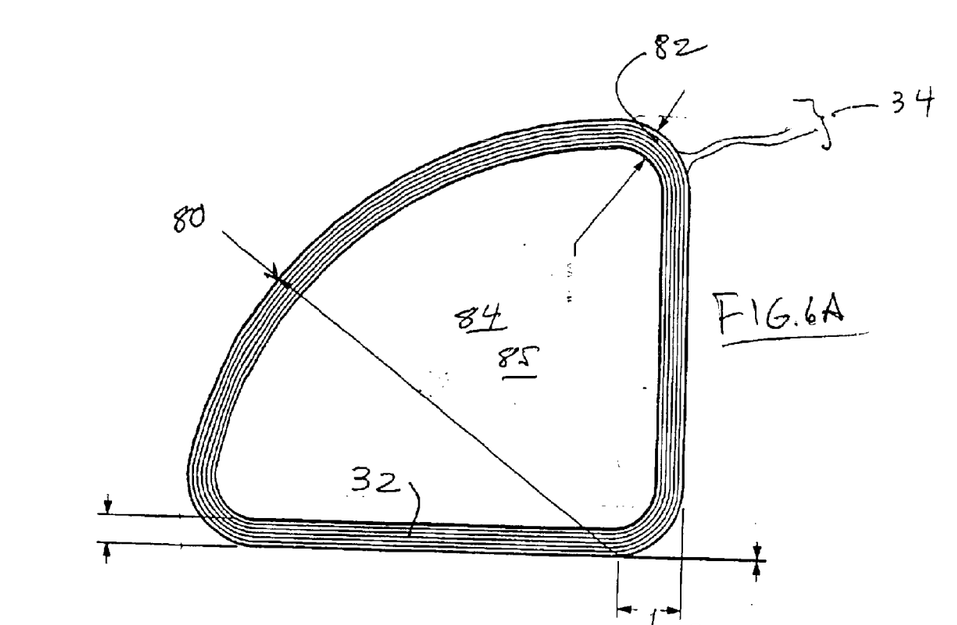
FIG. 6A is a plan view and FIG. 6B is a side view of an air-core antenna according to a preferred embodiment of the present invention.
Figure 6B:
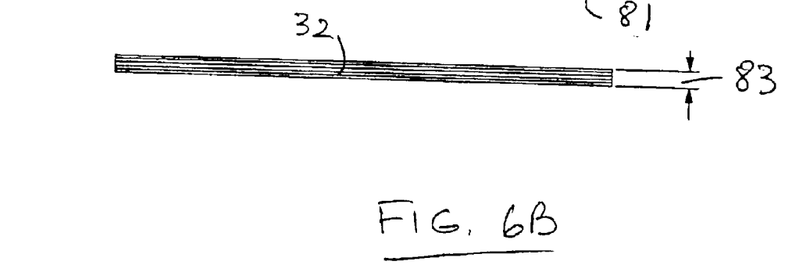
Figure 7:
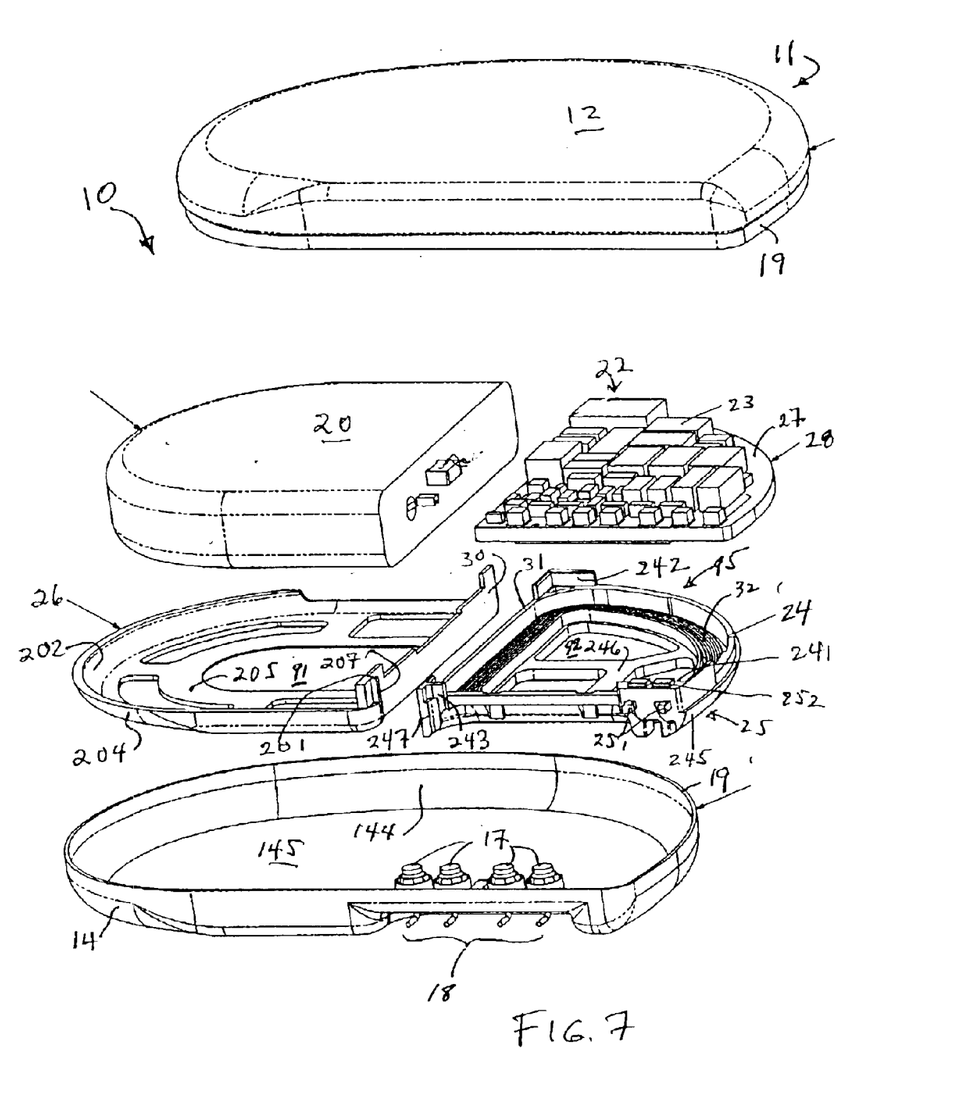
FIG. 7 is an exploded perspective view of the device of FIGS. 1–6 showing further details of the design and interrelationship of the various parts.

FIG. 5 is a partially exploded view of support structure 24 and antenna coil 32. Alignment of antenna coil 32 within support structure 24 is assured by quarter-elliptical shaped ridges 40, 41. Referring now to FIGS. 5–7, ridge 40 fits inside antenna coil 32 and ridge 41 lies outside of antenna coil 32. Together ridges 40, 41 and bottom portion 43 of support structure 24 form a channel into which antenna coil 32 is easily placed and affixed, for example, by an adhesive.

Referring again to FIG. 5, antenna coil 32 includes leads 34 that are electrically coupled to contacts 25 contained in support structure 24. It is convenient that support structure 24 has leads 25 with portions 252 for connection to circuit board 27 by any convenient means and portions 251 to which leads 34 of coil 32 are connected in any convenient manner. Soldering and wire bonding are non-limiting examples of suitable connection techniques. Solder dipping is preferred for attachment of leads 34 to contact portions 251, but other electrical attachment means well known in the art can also be used.

Referring now to FIG. 6A, antenna coil 32 conveniently has a quarter-ellipse like shape in plan view, with rounded corners. As used herein, the words "quarter-elliptical" and "quarter-ellipse" are intended to refer to this general overall shape including the rounded corners. Antenna coil 32 may be wound in any convenient manner, but use of a mandrel is preferred because of the ease with which a coil of a specific size and shape and number of turns may be formed. This is desirable so that coil 32 fits easily into and aligns with support structure 24. It is preferred to use highly conductive wire that has an insulating skin containing or is coated with an adhesive so that after being wound, coil 32 can be cured so that the various turns stick together to form a substantially rigid multi-layer coil that does not easily shed turns. This facilitates assembly of antenna coil 32 into support structure 24. Those of skill in the art will understand how to select coil wire, insulation and adhesive to suit their particular application and manufacturing process.

In a typical application where it is desired to communicate to or from device 10 using electromagnetic waves in a frequency range of roughly $10^5$ to $10^6$ Hertz, antenna coil 32 had a generally flat or pancake-like quarter-elliptical shape. Antenna coil 32 was formed of about 253 turns of 44 AWG copper magnet wire with Nylon™ insulation and a curable epoxy overcoat. Antenna coil 32 was wound on a quarter-elliptical shaped mandrel having a circular radius 80 of approximately 17.6 mm offset along one axis of the ellipse by amount 81 so that one side of the quarter-ellipse was about ten percent (~1.6 mm) longer than the other side in plan view, that is, when viewed looking in a direction perpendicular to the plane of the coil. The coil was about 1.35 mm thick in the plane of the coil as indicated by reference number 82 in FIG. 6A and about 0.76 mm thick perpendicular to the plane of the coil as indicated by reference number 83 in FIG. 6B. The start and end terminations of the coil (leads 34) were located where the shorter side met the circular arc of the coil. Such a coil had a DC resistance of about 130–190 ohms, a parallel resonant frequency of about 0.75–1.32 MHz in air, a Q of about 15–21 and an inductance of about 2.25–3.44 mH measured in air at 175 kHz and was suitable for use in the above-described implantable device. Persons of skill in the art will understand that the above-described coil is merely exemplary and that coils of other dimensions and shapes and electrical properties can be used as may be required by the particular application, without departing from the present invention.

It is known in the prior art to use a spiral wound single-layer antenna coil or other shape formed, for example, by etching of a copper sheet bonded to an insulated backing. All of the turns or leads of such a single-layer coil are in the same plane and/or lie on a common surface. It will be noted that antenna coil 32 of the present invention has multiple turns not all lying on the same plane or common surface, that is, the turns of the antenna coil of the present invention are not all coplanar and do not lie on a common surface. Two or more layers of turns are stacked one above the other in a direction perpendicular to the principal plane of the coil. As used herein, the words "multi-layer" with respect to antenna coil 32 are intended to refer to this arrangement as distinguished from single-layer coils of the prior art.

It will be further noted that air-core area 84 within coil 32 in plan view is a substantial fraction of total plan view area 85 of coil 32 (see FIG. 6A). The air-core area is determined by measuring the area within the inner perimeter of coil 32 in FIG. 6A and the total plan view area is determine by measuring the total coil area within the outer perimeter of coil 32 in FIG. 6A. The total plan view area includes the air-core area plus the annular area of the coil windings themselves. It is desirable that air-core area 84 be at least approximately fifty percent, conveniently approximately sixty percent and preferable approximately seventy to seventy-five percent of total plan view area 85 of coil 32. This is contrast to typical spiral-wound uni-planar antennas where the air-core area is usually a much smaller fraction of the total coil area.

FIG. 7 is an exploded perspective view of device 10 of FIGS. 1–2 showing further details of the interrelationship of the various parts. Coil 32 is wound, cured and placed in support structure 24 prior to support structure 24 being placed into lower housing half 14. Coil 32 is fixed in support structure 24 by an adhesive, for example, a curable epoxy. Lower half 14 of housing 11 receives support structure 24 containing coil 32, and support structure 26.

Referring now also to FIG. 4, adhesive 90 is applied over support structure 24 containing coil 32 and support structure 26 so that it flows through open regions 92, 91 in support structures 24, 26 to contact lower housing half 14. Some of adhesive 90 will also flow between support structures 24, 26 and housing half 14.

Battery 20 is placed into support structure 26 and module 28 is placed into support structure 24 above coil 32 so that all are in contact with the adhesive 90. When adhesive 90 is cured support structures 24, 26, coil 32, module 28, and battery 20 are thereby held firmly in place within housing 11. Suitable adhesives are well known in the electronics art, as for example epoxy resins, but other adhesives may also be used. A desiccant (not shown) is desirably included within housing 11 prior to its being hermetically sealed along joint 19.

Support structures 24, 26 are desirably formed of insulating material, as for example electronic grade plastic, but other insulating materials can also be used. Any convenient means may be used to form support structures 24, 26, as for example, but not limited to die casting, injection molding and machining. It is preferred that contacts 25 be insert molded within support structure 24 so that portions 251 of contacts 25 are conveniently located to receive leads 34 of coil 32 and portions 252 of contacts 25 are conveniently located so as to provide bonding surfaces to which electrical connections (e.g., wire bonds) may be attached from module 28. Coil leads 34 are preferably solder attached to contact portions 251 after coil 32 is glued into support structure 24 and before support structure-coil combination 95 is placed in housing 11. However, other attachment methods may also be used.

Referring again to FIG. 7, support structures 24, 26 have side and bottom portions 245, 246 and 204, 205 respectively, that mate with side and bottom portions 144, 145 of lower housing half 14. Side portions 245, 204 of support structures 24, 26 desirably have a radius of curvature that matches that of side portion 144 of housing half 14 and bottom portions 246, 205 have a contour (e.g., a substantially flat plane) that matches bottom portion 145 of housing half 14. This transfers the inertial weight of battery 20 and antenna 32 and module 28 as uniformly as possible to housing 11, thereby improving the ruggedness of the overall assembly. Support structures 24, 26 desirably have open regions 92, 91 in their respective bottom portions 246, 205 to reduce weight and cost and to allow mounting adhesive 90 to penetrate to inner surface 145 of housing-half 14 after support structures 24, 26 have been placed in housing-half 14.

Referring to FIGS. 3–5 and 7, it will be noted that support structures 24, 26 mate along surfaces 30, 31 and that circuit board 27 of module 28 is located and aligned in support structure 24 by tabs or portions 241–243 and that battery 20 is located and aligned in battery support structure 26 by portions 201–202. Further, support structures 24, 26 have thereon alignment tabs or portions 247, 207 respectively that when surfaces 30, 31 are joined, align structures 24, 26 in a predetermined position with respect to each other.

It is preferred that coil 32, module 28 and battery 20 be supported by a two-piece support structure, that is support structure 24 for antenna coil 32 and module 28 and support structure 26 for battery 20, but this is not essential. It will also be noted that mating surfaces 30, 31 where support structures 24, 26 join provide a transverse rib running across module 11, thereby enhancing the stiffness of module 11.

With respect to structures 24, 26, the words "support", "cup", "insulating member", etc., are intended to be used interchangeably and refer generally to the structure described herein. While structures 24, 26 each have the general shape of a shallow cup with a bottom portion and one or more curved and/or straight side portions extending away from the bottom portion, this is not intended to be limiting. Those of skill in the art will appreciate that, based on the description herein, the functions accomplished by structures 24, 26 can also be achieved by structures of different detailed design provided that, as a whole, such alternative structures provide substantially equivalent support and alignment functions for antenna 32, module 28 and battery 20.

Figure 8:
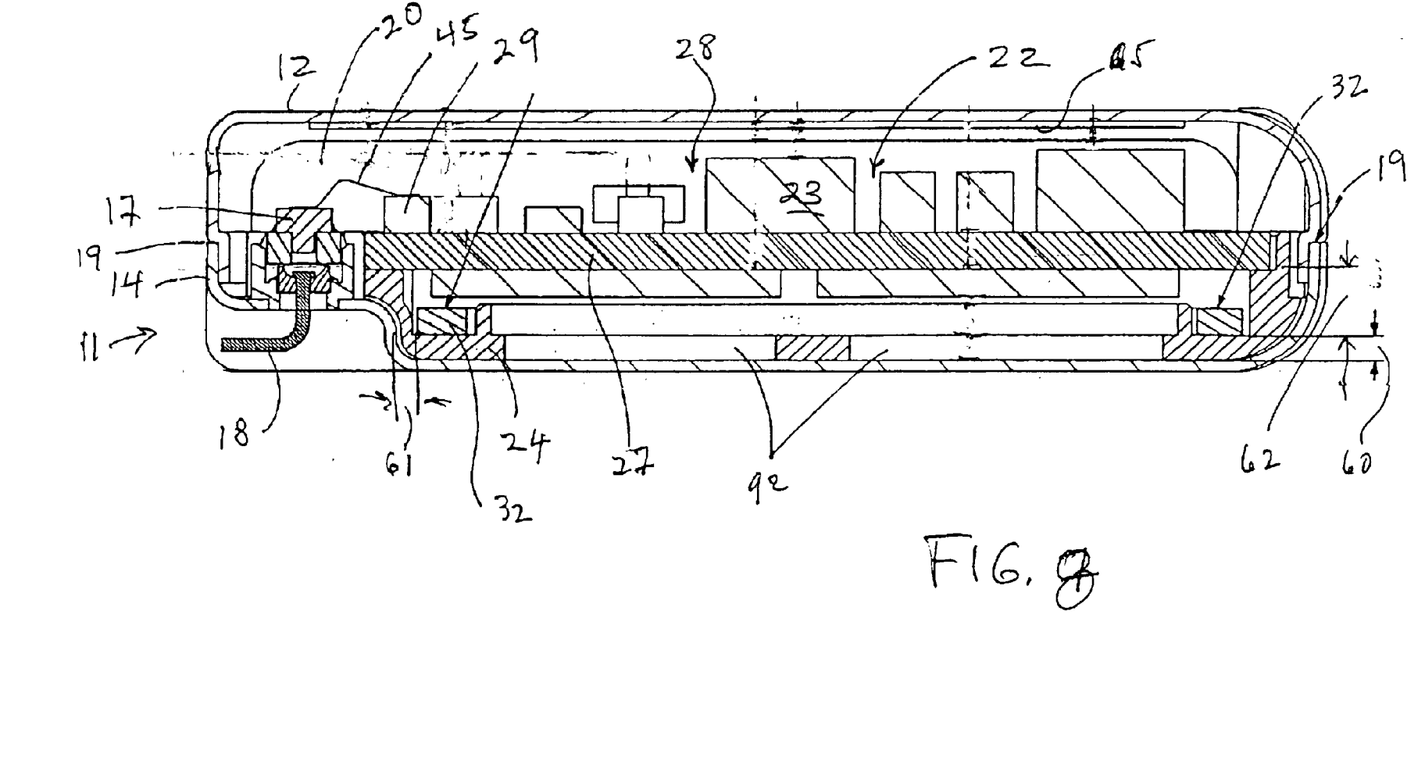
FIG. 8 is a cross-sectional view through a portion of the device of FIG. 3.

FIG. 8 is a cross-sectional view through a portion of the device of FIG. 3 along line A—A showing portions of circuit board 27, module 28, antenna 32, and support structure 24 when assembled within upper and lower halves 12, 14 of housing 11 and illustrating further details. The same reference numbers are used to identify the same elements as in FIGS. 1–7. Battery insulating layer 65, visible in FIG. 8, is conveniently attached to the inner surface of upper half 12 of housing 11 to prevent electrical contact between battery 20 and housing 11 if housing 11 is compressed after assembly.

It will be noted that support structure 24 locates contacts 29 on circuit board 27 at substantially the same height as feed-through contacts 17 in housing 11 so that wires 45 may be more easily and more efficiently connected there between. Further, as can be seen in FIG. 3, contacts 29 are also conveniently located with respect to contacts 17 in plan view, further facilitating interconnection thereof. In addition, support structure 24 locates portions 252 of contacts 25 for coupling antenna coil 32 to contacts 29 in substantially the same elevation and plan view location as feedthrough contacts 17 so that electrical coupling of antenna 32 to module 28 may be efficiently accomplished at the same time as connections are provided between contacts 29 and 17. This reduces the cost of manufacture of the overall device.

It will be noted in FIG. 8 that antenna coil 32 is spaced apart from housing 11 by distances 60, 61 and from substrate 27 by distance 62. It is desirable that distance 60 between a principal plane of coil 32 and a principal plane of housing 11 and distance 62 between a principal plane of coil 32 and a principal plane module substrate 27 be usefully approximately 0.5 mm or larger, conveniently approximately 0.7 mm or larger, and preferably approximately 0.76 mm or larger. The efficiency of antenna coil 32 degrades as the plane of coil 32 approaches closer to the plane of conductive housing 11 and/or the conductive portions of module substrate 27. The distances between the corners of coil 32 and housing 11, e.g., distance 61, is less important and can be smaller than distances 60, 62.

Thus there has been provided an implantable device with a multi-layer air-core antenna and support structures for the antenna, an electronic module for providing the desired stimuli and/or biological monitoring and communications, and an energy source for powering the unit, all in a compact and rugged housing, and which are conveniently and economically assembled and interconnected within the housing. Alignment and support of the parts is assured by the features of the insulating support cup or cups used for the antenna and the module and for the battery. The support cups conform to the interior of the housing and contain alignment tabs and surfaces so that when assembled they are aligned and located in predetermined positions within the housing and with respect to each other, and the battery, the antenna and the electronic module are also aligned and properly positioned in predetermined locations. This facilitates automated assembly and contributes to the ruggedness of the overall device. Further the antenna and module support cup desirably but not essentially includes insert-molded contacts having first contact regions optimized for connection to the antenna leads and second contact regions optimized for connection to the electronic module so that, if desired, different attachment methods may be used for the different connections.

Further the quarter-elliptical shaped design of the antenna takes maximum advantage of the available interior space within the module so as to provide the maximum antenna area and thereby more efficient coupling of electromagnetic waves through the housing. The mating quarter-elliptical shape of the support structure and the electronics module provides for proper alignment of the parts and locates leads or contacts on the antenna, support structure and module in close proximity to the external feed-throughs so that sensing or stimuli signals may be easily passed through the housing to or from the body in which the device is located. The contact regions on the circuit board and the external feed-throughs are placed at approximately comparable heights within the module to facilitate electrical connection there between. This greatly improves the manufacturability of the device.

Finally, the combination of the antenna/module support structure and the battery support structure self-align to each other and within the housing so that all of the parts that must be electrically interconnected have their contact regions substantially co-located for easy connection while at the same time providing an air-core antenna of maximum area within the space constraints of the housing.

While the preferred embodiments have been presented in the foregoing detailed description, it will be understood by those of skill in the art that many variations of the embodiments exist based on the information provided herein. For example, while cup-shaped support structures with curved sides are shown herein, which match the curved sides of the housing, other shapes can easily be used to match housings of different shapes. Further, while a quarter-elliptical coil shape is preferred for the present housing, other coil shapes can also be used depending upon the shape of the external housing. In addition, while a two-piece support structure is described herein, that is, one piece for the coil/module combination another piece for the battery, those of skill in the art will appreciate that a one-piece support structure can also be used so that coil, module and battery are supported by a single insulating member.

It should also be appreciated that the preferred embodiments are only examples, and are not intended to limit the scope, applicability, or configuration of the invention in any way. Rather, the foregoing detailed description provides those of skill in the art with a convenient roadmap for implementing the preferred exemplary embodiments of the invention. Various changes may be made in the function and arrangement described in connection with the exemplary preferred embodiments without departing from the spirit and scope of the invention as set forth in the appended claims.

What is claimed is:

1. An implantable medical device, comprising:
   an enclosure;
   a multi-layer air-core antenna having a plurality of coil windings, wherein each coil winding forms a separate layer disposed in its own plane and wherein said coil windings are stacked one above the other in a direction perpendicular to the planes of said plurality of coil windings in a helix arrangement; and
   a support cup within the enclosure retaining the antenna in a predetermined position within the enclosure.

2. The device of claim 1 wherein the support cup includes an outer surface that conforms at least in part to a portion of the inner surface of the enclosure.

3. The device of claim 1 wherein the support cup includes electrical contacts for receiving connections from the antenna and the electrical circuitry to electrically couple the antenna and an electrical circuitry.

4. The device of claim 1 wherein the support cup further comprises a first portion for retaining the antenna in predetermined relation thereto and a second portion for spacing a surface of the antenna a predetermined distance from the inner surface of the enclosure.

5. The device of claim 4 wherein the predetermined distance is approximately greater than or equal to 0.5 mm.

6. The device of claim 1 wherein the antenna includes a substantial quarter-elliptical plan view shape.

7. The device of claim 1 further comprising a support member for the energy source, wherein the support cup and the support member include mating structural alignment regions.

8. The device of claim 7 wherein the support cup and the support member position the electrical circuitry, the antenna and the energy source in predetermined relationship.

9. The device of claim 1 wherein the antenna, the support cup includes a substantially quarter-elliptical plan view shape.

10. The device of claim 1 further comprising electrical circuitry mounted on a substrate and a first insulating member aligns the antenna with respect to the enclosure and aligns the substrate with respect to the antenna, to thereby maintain predetermined minimum spacings between the substrate, the antenna and the enclosure, and the antenna being positioned substantially between the substrate and the enclosure.

11. The device of claim 10 wherein the minimum spacings include dimensions of approximately 0.5 mm or larger.

12. The implantable medical device of claim 1, wherein the multi-layer air-core antenna has a second plurality of coil windings overlaying the first plurality of coil windings, wherein each coil winding forms a separate layer disposed in its own plane and wherein said coil windings are stacked one above the other in a direction perpendicular to the planes of said plurality of coil windings.

13. An implantable device comprising a sealable housing, an electronic module, a multi-layer air-core antenna electrically coupled to the module and having a plurality of coil windings, wherein each coil winding forms a separate layer disposed in its own plane and wherein said coil windings are stacked one above the other in a direction perpendicular to the planes of said plurality of coil windings in a helix arrangement, and a first support cup for locating both the module and the antenna within the housing, the first cup having a first portion for receiving the antenna in spaced-apart relationship to the housing and a second portion for receiving the module in spaced-apart relationship to the antenna to thereby position the module substantially superimposed over the antenna.

14. The device of claim 13 wherein the first cup, the module and the antenna include substantially quarter-elliptical plan view shapes.

15. The device of claim 13 wherein a plane of the antenna is positioned a first minimum distance from a plane of the housing and a second minimum distance from a plane of the module, and the first and second minimum distances approximately 0.7 mm.

16. The device of claim 13 further comprising an energy source within the housing and a second insulating cup for positioning the energy source in spaced-apart relationship from the housing, wherein the first and second cups include corresponding mating regions wherein the first and second cups align with respect to each other within the housing.

17. The device of claim 13 wherein the housing further comprises first electrical connections extending through the housing and the module further comprises second electrical connections, wherein the first cup positions the module and the antenna within the housing in a predetermined arrangement wherein the first and second connections include substantially proximate structural arrangement.

18. The device of claim 17 wherein the first cup comprises electrical connections having first portions for receiving electrical connections from the antenna and second portions for receiving electrical connections from the module, and wherein a first outer surface of the second portions and a second outer surface of the second electrical structures include approximately co-planar connections.

19. An implantable device comprising a housing, an electronic module, an air-core antenna electrically coupled to the module, and an insulating cup for locating both the module and the antenna within the housing, the cup having a first portion for receiving the antenna in spaced-apart relationship to the housing and a second portion for receiving the module in spaced-apart relationship to the antenna, wherein the antenna includes a multi-turn coil having a plurality of coil windings, wherein each coil winding forms a separate layer disposed in its own plane and wherein said coil windings are stacked one above the other in a direction perpendicular to the planes of said plurality of coil windings in a helix arrangement and comprising a total area and an interior air-core area, wherein the air-core area includes greater than half of the total area.

20. The device of claim 19 wherein the module and a first interior surface of the housing include a structural arrangement of the antenna located substantially therebetween.

* * * * *